US011433031B2

(12) United States Patent
Sakamoto et al.

(10) Patent No.: US 11,433,031 B2
(45) Date of Patent: *Sep. 6, 2022

(54) METHOD FOR MANUFACTURING ACETAMINOPHEN PREPARATION

(71) Applicant: NIPPON ZOKI PHARMACEUTICAL CO., LTD., Osaka (JP)

(72) Inventors: Hiroshi Sakamoto, Sakai (JP); Kunio Komai, Fuchu (JP); Kenji Sakakibara, Ono (JP); Hirokazu Banba, Ono (JP); Kiyoshi Fukuda, Ono (JP)

(73) Assignee: NIPPON ZOKI PHARMACEUTICAL CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/222,237

(22) Filed: Apr. 5, 2021

(65) Prior Publication Data

US 2021/0220283 A1    Jul. 22, 2021

Related U.S. Application Data

(62) Division of application No. 16/099,961, filed as application No. PCT/JP2017/017603 on May 9, 2017, now Pat. No. 11,033,501.

(30) Foreign Application Priority Data

| May 10, 2016 | (JP) | JP2016-094764 |
| Aug. 26, 2016 | (JP) | JP2016-165993 |
| Oct. 13, 2016 | (JP) | JP2016-201560 |

(51) Int. Cl.
| *A61K 9/20* | (2006.01) |
| *A61K 47/02* | (2006.01) |
| *A61K 47/10* | (2017.01) |
| *A61K 31/167* | (2006.01) |
| *A61K 47/30* | (2006.01) |
| *A61K 47/38* | (2006.01) |
| *A61K 47/32* | (2006.01) |
| *A61K 47/26* | (2006.01) |
| *A61K 47/20* | (2006.01) |

(52) U.S. Cl.
CPC .............. *A61K 9/2095* (2013.01); *A61K 9/20* (2013.01); *A61K 9/2054* (2013.01); *A61K 31/167* (2013.01); *A61K 47/02* (2013.01); *A61K 47/10* (2013.01); *A61K 47/20* (2013.01); *A61K 47/26* (2013.01); *A61K 47/30* (2013.01); *A61K 47/32* (2013.01); *A61K 47/38* (2013.01)

(58) Field of Classification Search
CPC .. A61K 9/2095; A61K 9/2054; A61K 31/167; A61K 47/02; A61K 47/10; A61K 47/20
See application file for complete search history.

(56) References Cited

U.S. PATENT DOCUMENTS

| 2001/0044472 A1 | 11/2001 | Upadhyay et al. |
| 2012/0129878 A1 | 5/2012 | Murakawa et al. |

FOREIGN PATENT DOCUMENTS

| CN | 102548556 A | 7/2012 |
| EP | 1 161 941 A1 | 12/2001 |
| JP | S61-145111 A | 7/1986 |
| JP | H10-506412 A | 6/1998 |
| JP | 2003-081876 A | 3/2003 |
| JP | 2003-509368 A | 3/2003 |
| JP | 2012-144520 A | 8/2012 |
| WO | 97/017947 A1 | 5/1997 |
| WO | 00/54752 A1 | 9/2000 |
| WO | 2001/019363 A1 | 3/2001 |
| WO | 2010/081722 A2 | 7/2010 |

OTHER PUBLICATIONS

Japanese Pharmaceutical Excipients Directory 2007, Yakuji Nippo Ltd., pp. 65, 67, 68, 93, 100, 101, 181, 281, 282 and 318.
Jun. 6, 2017 International Search Report issued in International Patent Application No. PCT/JP2017/017603.
Nov. 13, 2018 International Preliminary Reporton Patentability issued in International Patent Application No. PCT/JP2017/017603.
Feb. 13, 2018 Decision to Grant a Patent issued in Japanese Application No. 2017-545607.
Dec. 5, 2017 Office Action issued in Japanese Application No. 2017-545607.
Nov. 11, 2019 Search Report issued in European Patent Application No. 17796157.0.
Bowen; "Particle Size Distribution Measurement from Millimeters to Nanometers and from Rods to Platelets;" Journal of Dispersion Science and Technology; vol. 23, No. 5; pp. 631-662; 2002.

*Primary Examiner* — Snigdha Maewall
(74) *Attorney, Agent, or Firm* — Oliff PLC

(57) ABSTRACT

A method for manufacturing a preparation which contains acetaminophen at a high content, in particular, a miniaturized tablet (conventional tablets, sustained-release tablets, etc.) which have excellent elution properties, preferable hardness and high drug content uniformity, and a premix drug substance of acetaminophen which has improved manufacturability. According to the method in which acetaminophen having a preset particle size is used for manufacturing a preparation, the flowability of acetaminophen can be improved so that secondary agglomeration can be suppressed and manufacturing efficiency can be elevated. Thus, this method is highly useful for manufacturing an acetaminophen preparation having improved administrability, for example, a reduced size.

4 Claims, 1 Drawing Sheet

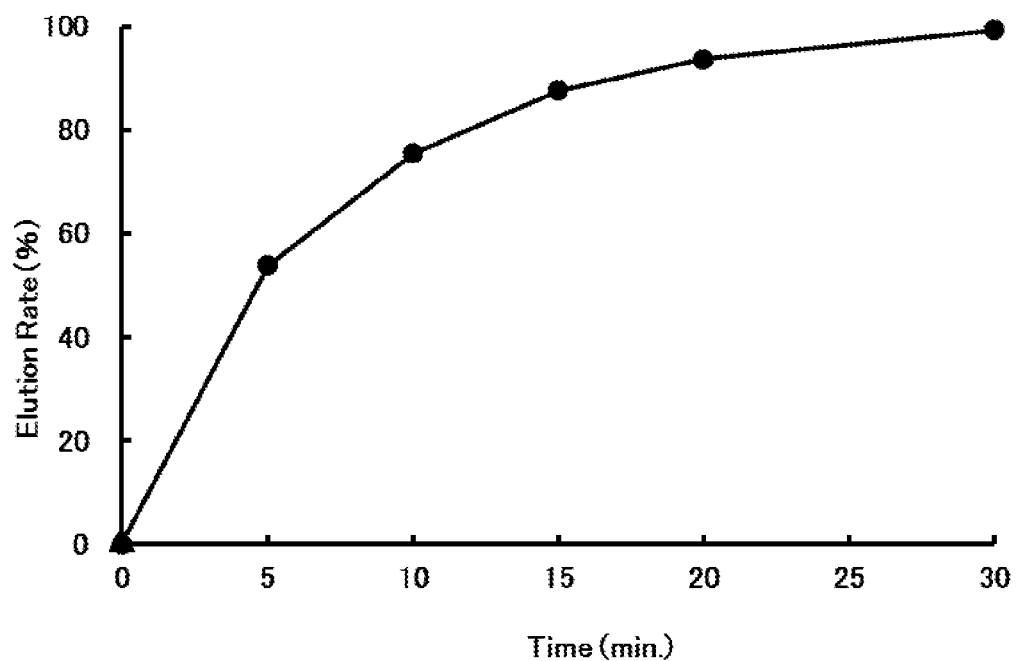

METHOD FOR MANUFACTURING ACETAMINOPHEN PREPARATION

CROSS REFERENCE TO RELATED APPLICATION

This application is a division of U.S. application Ser. No. 16/099,961, filed Nov. 8, 2018, the contents of which are incorporated herein by reference.

TECHNICAL FIELD

The present invention relates to a method for manufacturing a preparation using acetaminophen having a specified particle size distribution as mentioned below (where the acetaminophen is also referred to as "the present acetaminophen", hereinafter).

BACKGROUND ART

A preparation, e.g., a drug, is manufactured through various preparation processes. In order to make it possible to exert the functions of a preparation satisfactorily, it is needed to select the most suitable manufacturing method with taking various factors into consideration and to examine a preparation machine, the conditions for the operation of the preparation machine, and the like. The method for manufacturing a preparation having the dosage form of tablets is roughly classified into a dry direct compression method, a dry granulation method (e.g., a dry roller compactor method, a roll granulator method) and a wet granulation method (e.g., a spray granulation method, an agitation granulation method, an extrusion granulation method, a fluidized bed granulation method). These methods have their own disadvantages and advantages in association with the number of manufacturing steps, the manufacturing speed, economic advantages, the degree of achievement of desired properties of the preparation, and the like. Therefore, these methods have to be selected depending on the intended use.

For example, a dry roller compactor method, which is one type of the dry granulation method, is a making method of the tablet in which additives are blended into a drug, the resultant mixture is compression-molded in a flaky form, is then deagglomerated and/or sized, and is then classified by the particle size, and the resultant fine powder is compressed again. However, a large amount of powder is spread during the deagglomeration and/or sizing and therefore the yield is poor, and it is needed to carry out a compression step once and therefore the hardness of the tablets may be deteriorated (Japanese Translation of PCT International Publication No. 2000-506540). An agitation granulation method, which is one type of the wet granulation method, is a method in which a drug and additives are introduced into a granulation vessel and are mixed together by the rotation of an impeller, and a binder solution is added dropwise to or sprayed thereonto to granulate the mixture in a properly wet state. In this method, however, the dispersion of the binder solution may become inhomogeneous. Therefore, the resultant granule product may become partially hard, there are a slightly large amount of ungranulated powder particles, and the content uniformity may also be slightly poor. For these reasons, it is needed to perform wet deagglomeration and/or sizing and then drying, and the number of steps may increase and the hardness of the tablets may be deteriorated.

A dry direct tableting method (also referred to as "a dry direct compression method") is the simplest method in which a drug and additives are simply mixed without any modification and the resultant mixture is compressed into tablets. In the dry direct compression method, a method is also included, in which additives are prepared in the form of a solution in advance, then the solution is subjected to a dry treatment for direct compression purposes using a spray drier or the like, then a drug powder is blended into the resultant particles and then the mixture is compressed into tablets. This method has many steps, because a wet-mode process is employed as a pretreatment. In contrast, a dry direct compression method has fewest preparation steps and therefore has such advantages that the cost for manufacturing can be reduced and the speed of manufacturing is high, because granules are not produced in this method. However, in a dry direct compression method, the flowability of a powder to be mixed is poor compared with those achieved in a dry granulation method and a wet granulation method in each of which granules are produced, and therefore there are disadvantages such as the increase in the mass variation and the occurrence of a trouble in compression moldability. A dry direct compression method has been employed frequently in Europe and the United States before the 1970s in which the particle diameters of drugs and additives are relatively large and the problem of secondary agglomeration is not so serious. In recent years, however, there have been developed many hardly-soluble drugs. In hardly-soluble drugs, secondary agglomeration tends to occur when finely pulverized using a pin mill, a jet mill, or the like, and there is a problem with the content uniformity. For these reasons, the dry direct compression method has been rarely used these days.

For the above-mentioned reasons, a fluidized bed granulation method, which is one type of a wet granulation method, has been generally employed most frequently in the present day (Japanese Patent Laid-Open No. 2013-216610, Japanese Translation of PCT International Publication No. 2015-63521). In a fluidized bed granulation method, a drug and additives are introduced into a fluidized bed granulator to fluidize these components and a binder solution or a binder solution prepared by dissolving or suspending a drug is added by spraying. This method has excellent content uniformity and high yield and enables the manufacture of granules suitable for tablet compression, and therefore has been employed frequently these days. However, the sizes of particles of a recent hardly-flowable drug are small. If there is a difference in particle diameter or mass between the drug and an additive, the drug may be air-classified, sometimes resulting in the deterioration in content uniformity. Therefore, considerable skill is required for the operation technique.

Acetaminophen is an antipyretic and analgesic agent that has been used widely and traditionally, and is a highly safe drug and can be administered to children as well as adults. The use and dose of acetaminophen for ethical use is as follows: for the relief of headache, low back pain and the like in an adult, oral administration at a dose of 300 to 1000 mg per one shot in terms of acetaminophen content, with the limit of the total dose of 4000 mg per day, at 4- to 6-hour or longer intervals. In the currently commercially available acetaminophen tablets, there are three types, i.e., 500-mg tablets, 300-mg tablets and 200-mg tablets, depending on the amount of the active ingredient. Due to the high content of the drug in the tablets, the tablets become relatively large. In addition, sustained release tablets having a long-lasting effect have not been commercially available yet. Therefore, the tables have to be administered several times per day. In these situations, the development of tablets which have smaller sizes and more preferably can be administered only twice, i.e., in the morning and evening, daily has been demanded by physicians in clinical settings and patients for the purpose of improving QOL or compliance. In addition, acetaminophen has a characteristic bitter taste, and therefore an ingenuity in the manufacture of a preparation, such as masking for reducing the bitter taste, has been also demanded.

In Japan, on the other hand, acetaminophen has a very inexpensive drug price (500-mg tablets: 9.80 yen/tablet, 300-mg tablets: 8.50 yean/tablet, 200-mg tablets: 7.60 yen/tablet), and therefore it is required to reduce the cost for the manufacturing the tablets. Thus, the selection and ingenuity of raw materials and manufacturing methods are the problems to be overcome. In particular, most of the prices of additives to be blended are equal to or higher by several times than the price of acetaminophen, and therefore the reduction or elimination of additives is critical for the problem of reduction in manufacturing cost.

As the method for manufacturing a drug preparation, a fluidized bed granulation method is most frequently employed, as mentioned above. In this method, however, it is needed to blend relatively many kinds of additives for the purpose of improving flowability, moldability, and the like, and therefore it is difficult to reduce the sizes of tablets. Furthermore, the fluidized bed granulation method is a method in which granules are prepared by wet granulation, then a lubricant and the like are added to the granules and then the resultant granules are compressed into tablets. Therefore, the number of steps is increased, and the cost for manufacturing becomes relatively high. In the dry direct compression method, in contrast, a mixed powder is directly compressed, and therefore the number of steps is reduced and the cost for manufacturing is also reduced. In this method, however, the flowability of the mixed powder is poor compared with a dry granulation method or a wet granulation method in each of which granules are manufactured, and therefore the mass variation may increase and the compression moldability may be deteriorated.

In particular, acetaminophen has an extremely high secondary agglomeration force associated with an intermolecular force (van der Waals force), electrostatic charging and the like, and is in the form of a powder having extremely poor flowability and complicated particle shapes. For these reasons, the dry direct compression method has been rarely employed for the manufacture of an acetaminophen preparation. Particularly for improving the flowability of acetaminophen, it is needed to blend additives in a large amount, and therefore the dry direct compression method has been rarely employed when it is intended to reduce the sizes of tablets.

Acetaminophen crystals manufactured in a crystallization step in the manufacture of a drug substance in a drug substance manufacturer cannot be regulated with respect to the hardness of the crystals and the particle diameters of the crystals due to the size of an apparatus to be used, the outside air conditions that vary with the seasons and the like. Therefore, it is needed to pulverize the generated crystals to obtain uniform crystals. However, when acetaminophen having various levels of hardness and various particle diameters are pulverized uniformly using a pin mill, a hummer mill, or the like, acetaminophen having a smaller particle diameter is often pulverized excessively. A fine powder generated by the pulverization has large surface areas and therefore has enhanced electrostatic charging properties, resulting in further deterioration in flowability. As a result, the adhesion of the particles onto the inner surface of the apparatus is also increased, which is a major cause of the deterioration in work efficiency. Furthermore, when the pulverizing treatment is carried out, the shape of the particles and the particle size distribution of the particles also vary, and the behavior of secondary agglomeration also varies, resulting in the variation in elution rate of a final product (tablets).

The present inventors have considered using the present acetaminophen drug substance for the purpose of enabling the manufacture of a preparation by a dry direct compression method by improving the flowability of acetaminophen. Particularly, the present inventors have made extensive and intensive studies on tablets which are manufactured by blending additives into the present acetaminophen drug substance, then deagglomerating and/or sizing the resultant mixture to produce a powder and then compressing the deagglomerated and/or sized powder and a premix drug substance which is manufactured by deagglomerating and/or sizing a powder prepared by blending a dispersing agent and a solubilizing agent into the present acetaminophen drug substance. The present acetaminophen is an acetaminophen product that is not subjected to the below-mentioned pulverizing step, and therefore the present acetaminophen is also referred to as "unpulverized" acetaminophen, an "unpulverized product" of acetaminophen, or simply an "unpulverized product". In a precise sense, the present acetaminophen may be in any form as long as the particle size distribution falls within the below-mentioned range, and the present acetaminophen is not limited to a product that is not subjected to a pulverizing step.

The method for manufacturing an acetaminophen preparation by a dry direct compression method is disclosed in Patent Document 1. However, in Patent Document 1, there is found no statement about the matter that unpulverized acetaminophen is used as in the case of the present invention or the matter that a powder prepared by blending additives into acetaminophen is deagglomerated and/or sized. Particularly, acetaminophen is in the form of crystals or a crystalline powder, there are three types of crystal polymorphisms (types I, II, and III) are reported presently, and type II (i.e., long and thin needle-like) crystals are also included in the unpulverized acetaminophen to be used in the present invention. However, Patent Document 1 describes that the acetaminophen used in Patent Document 1 is preferably in a granular form, which is different from the form of the acetaminophen of the present application. In addition, it is described that the manufacturing method employed in Patent Document 1 is a direct compression method. However, the method employed in the section "Examples" is a method in which microcrystalline cellulose having a wet cake-like form is mixed with water to form a slurry having a solid content of about 15% as a pretreatment, then colloidal silicon dioxide is mixed with the slurry, the resultant mixture is spray-dried to produce aggregates in which microcrystalline cellulose and silicon dioxide are closely conjugated with each other, then acetaminophen and other additives are mixed with the aggregates, and then the resultant mixture is compressed into tablets. As mentioned above, the manufacturing method disclosed in Patent Document 1 is a direct compression method in which additives are prepared in a liquid form in advance and a drying treatment is carried out using a spray drier or the like for direct compression purposes. In the method, the pretreatment, which is a wet-mode method, is carried out, and therefore the number of steps is larger than that in a direct compression method in which a drug and additives are mixed together while keeping these components in powdery forms, and therefore it takes manufacturing cost and manufacturing time. In contrast, the manufacturing method of the present application is the simplest direct compression method in which the pretreatment is not required and a drug and additives are mixed and compressed in the form of powders.

In Patent Document 2, a method is disclosed, in which, when a drug and additives are mixed together as a preparative step in the manufacture of a preparation by a direct tableting method, a drug and a flowability modifier are mixed together in the case where the content of the drug in the drug preparation having an average particle diameter of 40 μm or less is as low as 20% by weight or less. In Patent Document 3, it is described that a medicinal-ingredient-containing surface-modified powder, which is manufactured by mixing a medicinal ingredient with a surface-modifying base material to modify the surfaces of the powder, has excellent flowability and enables the manufacture of tablets by a dry direct compression method. In the present invention, in contrast, only the mixing of a drug with a dispersant is insufficient and it is preferred to deagglomerate and/or size the mixture. In both of Patent Documents 2 and 3, there is found no statement about the matter that a powder composed of a drug and a dispersant (which corresponds to "a flowability modifier" used in Patent Document 2, and "a surface-modifying base material" used in Patent Document 3) is deagglomerated and/or sized.

PRIOR ART DOCUMENTS

Patent Documents

Patent Document 1: Japanese Translation of PCT International Publication No. H10-506412
Patent Document 2: Japanese Patent Laid-Open No. 2003-81876
Patent Document 3: International Publication No. WO00/54752

SUMMARY OF THE INVENTION

Problem to be Solved by the Invention

The problem to be achieved by the present invention is to provide a method for manufacturing: a preparation containing acetaminophen at a high content, particularly miniaturized tablets (conventional tablets, sustained release tablets, and the like) which have excellent elution properties, preferable hardness and high drug content uniformity and can be manufactured by a dry direct compression method; and a premix drug substance which has improved flowability and manufacturability and is composed of acetaminophen, a dispersant, and optionally a solubilizing agent. More specifically, the problem to be achieved by the present invention is to provide a method for manufacturing tablets, in which the electrostatic charging properties and flowability of acetaminophen are improved and therefore the manufacture can be achieved by a dry direct compression method that does not need to carry out a wet pretreatment, includes mixing a drug with additives while keeping the powdery forms thereof and then compressing the mixture into tablets, and is therefore the simplest method.

Means for Solving Problem

The present inventors have made intensive and extensive studies for the purpose of solving the above-mentioned problem, and it has been found that, in the manufacture of an acetaminophen preparation, the flowability and electrostatic charging properties of acetaminophen can be improved without requiring the use of many types of additives in large amounts, by using unpulverized acetaminophen as a drug substance and preferably by blending additives including a dispersant into acetaminophen and then deagglomerating and/or sizing the mixture. As a result, it has become possible to manufacture an acetaminophen preparation by a dry direct compression method which is the simplest method and has been believed to be hardly employed for the manufacture of an acetaminophen preparation. Particularly it has been found that, a preparation, such as miniaturized tablets and sustained-release tablets, which is improved in agglomeration properties and poor flowability characteristic to acetaminophen, has excellent elution properties and moldability and is bitter-taste-masked can be manufactured by selectively deagglomerating and/or sizing acetaminophen crystals having large particle diameters and agglomerated acetaminophen clusters using a deagglomerating and/or sizing machine to disperse and make adhere additives including a dispersant in and to the surfaces of the acetaminophen particles in a step of blending unpulverized acetaminophen with a dispersant and optionally a solubilizing agent and in a step of blending other additives into the mixture.

In a dry direct compression method, if the amounts of additives are reduced for the purpose of miniaturizing the tablets, moldability may be deteriorated and hardness may become insufficient. However, it has been found that tablets having excellent hardness can be manufactured by adding a small amount of water using an atomizer or the like to adjust the water content in the powder in the process of blending unpulverized acetaminophen with additives, particularly prior to the blending of water-soluble additives.

It has also been found that a premix drug substance having excellent productivity because the electrostatic charging properties and flowability of acetaminophen can be improved can be manufactured by blending unpulverized acetaminophen with a dispersant and optionally a solubilizing agent and then deagglomerating and/or sizing the mixture using a deagglomerating and/or sizing machine to disperse and make adhere the dispersant and the solubilizing agent in and onto the surfaces of acetaminophen particles. The present inventors have made further studies on the basis of these findings. As a result, the present invention has been accomplished.

That is, the present invention relates to the following items (1) to (30).

(1) A method for manufacturing a preparation using acetaminophen having a particle size distribution that d10 is 5 to 300 μm and d90 is 200 to 900 μm.

(2) The manufacturing method according to item (1), wherein the acetaminophen has the particle size distribution that d10 is 10 to 200 μm and d90 is 250 to 800 μm.

(3) The manufacturing method according to item (1) or (2), wherein the method includes a process including steps of; (a) blending a dispersant and optionally a solubilizing agent into the acetaminophen; (b) blending additives other than the dispersant, the solubilizing agent and a lubricant; and (c) blending a lubricant, wherein the preparation has the dosage form of tablets manufactured by a dry direct tableting method.

(4) The manufacturing method according to item (3), wherein the method further includes a step of carrying out deagglomeration and/or sizing to disperse and make adhere the additives in and onto the surfaces of the acetaminophen particles and the step is performed at least one time subsequent to any one step selected from steps (a) to (c).

(5) The manufacturing method according to item (3) or (4), wherein the blending ratio of the acetaminophen is 75 to 95% by weight relative to 100% by weight of the preparation.

(6) The manufacturing method according to any one of items (3) to (5), wherein the dispersant is hydrated silicon dioxide or light anhydrous silicic acid.

(7) The manufacturing method according to any one of items (3) to (6), wherein the blending ratio of the dispersant is 0.1 to 3% by weight relative to 100% by weight of the preparation.

(8) The manufacturing method according to any one of items (3) to (7), wherein the solubilizing agent is macrogol or sodium lauryl sulfate.

(9) The manufacturing method according to any one of items (3) to (8), wherein the blending ratio of the solubilizing agent is 0 to 0.8% by weight relative to 100% by weight of the preparation.

(10) The manufacturing method according to any one of items (3) to (9), wherein microcrystalline cellulose is included in the additives to be used in step (b).

(11) The manufacturing method according to item (10), wherein the blending ratio of microcrystalline cellulose is 1 to 10% by weight relative to 100% by weight of the preparation.

(12) The manufacturing method according to any one of items (3) to (11), wherein step (b) includes steps of;
(b-1) blending an insoluble additive and then adding water; and
(b-2) optionally blending a water-soluble additive.

(13) The manufacturing method according to item (12), wherein the addition ratio of water is 0.3 to 2.5% by weight relative to 100% by weight of the preparation.

(14) The manufacturing method according to item (12) or (13), wherein at least microcrystalline cellulose is contained as the insoluble additive.

(15) The manufacturing method according to item (14), wherein low substituted hydroxypropylcellulose or crospovidone is further contained as the insoluble additive.

(16) The manufacturing method according to item (15), wherein the addition ratio of low substituted hydroxypropylcellulose or crospovidone is 1 to 10% by weight relative to 100% by weight of the preparation.

(17) The manufacturing method according to any one of items (12) to (16), wherein the deagglomeration and/or sizing is carried out at least one time subsequent to step (a).

(18) The manufacturing method according to any one of items (3) to (17), wherein a sustained-release base material is included in the additives to be used in step (b).

(19) The manufacturing method according to item (18), wherein the sustained-release base material is at least one component selected from hypromellose, a carboxyvinyl polymer, and carboxymethylcellulose sodium salt.

(20) The manufacturing method according to item (18), wherein the sustained-release base material is composed of at least two components selected from hypromellose, a carboxyvinyl polymer, and carboxymethylcellulose sodium salt.

(21) The manufacturing method according to any one of items (18) to (20), wherein the blending ratio of the sustained-release base material is 1 to 15% by weight relative to 100% by weight of the preparation.

(22) The manufacturing method according to any one of items (18) to (21), wherein the deagglomeration and/or sizing is carried out at least one time subsequent to step (b).

(23) The manufacturing method according to item (1) or (2), wherein the preparation is a premix drug substance.

(24) The manufacturing method according to item (23), wherein the blending ratio of the acetaminophen is 90 to 99.9% by weight relative to 100% by weight of the preparation.

(25) The manufacturing method according to item (21) or (22), wherein hydrated silicon dioxide or light anhydrous silicic acid is contained as the dispersant.

(26) The manufacturing method according to item (25), wherein the blending ratio of the dispersant is 0.1 to 3% by weight relative to 100% by weight of the preparation.

(27) The manufacturing method according to item (25) or (26), wherein macrogol or sodium lauryl sulfate is contained as the solubilizing agent.

(28) The manufacturing method according to item (27), wherein the blending ratio of the solubilizing agent is 0 to 0.8% by weight relative to 100% by weight of the preparation.

(29) A preparation manufactured by the manufacturing method according to any one of items (1) to (28).

(30) The preparation according to item (29), wherein the preparation is a drug.

Advantages of the Invention

According to the manufacturing method of the present invention, a preparation having improved QOL and compliance, such as acetaminophen tablets that are miniaturized and have improved administerability and acetaminophen sustained-release tablets of which the number of doses per day is reduced compared with the conventional preparations, can be manufactured by a dry direct compression method that is the simplest method. Therefore, the time of manufacturing is shortened to improve the manufacturing efficiency, and the cost for manufacturing is also reduced. For these reasons, the manufacturing method of the present invention is very useful and is suitable for practical use.

BRIEF DESCRIPTION OF DRAWING

FIG. 1 is a graph illustrating the results of an elution test (until 30 minutes after the initiation of elution) of a preparation (acetaminophen content: 300 mg/tablet) manufactured by a manufacturing method of the present invention which is mentioned in Example 1.

MODE FOR CARRYING OUT THE INVENTION

The present invention relates to a method for manufacturing a preparation using acetaminophen which is unpulverized, i.e., has a specified particle size distribution as mentioned below.

The preparation manufactured by the manufacturing method of the present invention includes, but not limited to, tablets, capsules, a powder, granules, a liquid, a syrup, an injection, a suppository, an inhalation, a premix drug substance, and the like. The preparation of the present invention is preferably tablets and a premix drug substance, more preferably tablets.

In the present invention, the term "tablet" refers to a solid preparation having a certain form which can be used for oral administration, unless otherwise stated. The tablets include, in addition to the conventional tables, orally disintegrating tablets, chewable tablets, troche tablets, sublingual tablets, foamed tablets, dispersed tablets, dissolved tablets and sustained release tablets, and are preferably the conventional tablets and sustained release tablets, more preferably the conventional tablets. The tablets to be manufactured in the present invention include single-layer tablets each having a single-layer structure and multilayer tablets each having a multilayer structure having two or more layers, and are preferably single-layer tablets. The tablets according to the present invention include uncoated tablets (plain tablets), sugar-coated tablets, gelatin-encapsulated tablets, and film-coated tablets (including enteric coated tablets and stomach-soluble tablets) (which are also collectively named as "coated tablets", in contrast to uncoated tablets).

In the present invention, the term "premix drug substance" is not limited to a substance which is prepared by mixing a drug substance with an additive and can be sold as a mixed raw material product for use in the manufacture of preparation of a drug or the like, and includes all of mixtures each composed of a drug substance and an additive. The premix drug substance manufactured by the manufacturing method of the present invention contains acetaminophen at a high content, is improved in flowability and the like and has high manufacturability. Therefore, when tablets or the like are prepared using the premix drug substance, it becomes possible to reduce the kinds and amounts of additives and eliminate a granulation process, and therefore it becomes possible to manufacture miniaturized tablets having high acetaminophen content or reduce the cost for the manufacture of the tablets. It also becomes possible to manufacture a preparation such as tablets by the manufacturing method of the present invention using the premix drug substance.

Next, one example of the preferred embodiment of the manufacturing method of the present invention will be described.

(A) Tablets

[1] A dispersant and optionally a solubilizing agent are blended into an unpulverized product of acetaminophen.

[2] An insoluble additive is further blended into a powder obtained in step [1].

[3] If necessary, a water-soluble additive is further blended into a powder obtained in step [2].

[4] A lubricant is blended into a powder obtained in step [3].

[5] A powder obtained in step [4] is compressed into tablets.

In this process, deagglomeration and/or sizing is carried out at least one time using a deagglomerating and/or sizing machine subsequent to steps [1] to [4] to allow the additive such as the dispersant to be dispersed in and made to adhere to the surfaces of acetaminophen particles uniformly. If necessary, subsequent to step [1] or [2], water is added in an amount of 0.3 to 2.5% by weight, preferably 0.8 to 2.0% by weight, still more preferably 1.0 to 1.8% by weight, relative to 100% by weight of the tablets using an atomizer or the like to adjust the water content in the powder. Alternatively, depending on the circumstances, a solution prepared by dissolving a solubilizing agent, e.g., liquid polysorbate, in water may be used for the adjustment of the water content. The hardness of the tablets can be increased by adjusting the water content in this manner. When the adjustment of water content is not carried out, it is also possible to carry out steps [1] to [3] in one step, i.e., mix additives other than a lubricant with an unpulverized product of acetaminophen and deagglomerate and/or size the resultant mixture.

Examples of the insoluble additive to be used in the manufacturing method of the present invention include microcrystalline cellulose, low substituted hydroxypropyl-cellulose and crospovidone, and examples of the water-soluble additive include trehalose, hypromellose, a carboxyvinyl polymer, carboxymethylcellulose, carboxymethylethylcellulose, hydroxypropylcellulose, sodium alginate, a polyvinyl alcohol-acrylic acid-methyl methacrylate copolymer, gelatin, and sodium hydrogen carbonate.

(B) Premix Drug Substance

[1] A dispersant (e.g., hydrated silicon dioxide, light anhydrous silicic acid) and optionally a solubilizing agent (e.g., macrogol powder) are blended into an unpulverized product of acetaminophen.

[2] The powder obtained in step [1] is deagglomerated and/or sized using a deagglomerating and/or sizing machine, and an additive such as a dispersant is dispersed in and made to adhere to the surfaces of acetaminophen particles uniformly.

It is possible to use the premix drug substance as the resultant mixture in step [1] in the above-mentioned tablet manufacturing process.

One example of the more preferred embodiment of the manufacturing method of the present invention will be described.

(A-1) Conventional Tablets

[1] A dispersant (e.g., hydrated silicon dioxide, light anhydrous silicic acid) and optionally a solubilizing agent (e.g., macrogol powder) are blended into an unpulverized product of acetaminophen.

[2] The powder obtained in step [1] is deagglomerated and/or sized using a deagglomerating and/or sizing machine and an additive such as a dispersant is dispersed in and made to adhere to the surfaces of acetaminophen particles uniformly.

[3] An insoluble additive (e.g., microcrystalline cellulose, low substituted hydroxypropylcellulose, crospovidone) is further blended into the powder obtained in step [2].

[4] A small amount of water is added using an atomizer to and mixed with the powder obtained in step [3].

[5] A lubricant (e.g., magnesium stearate) is blended into the powder obtained in step [4], and the resultant mixture is compressed into tablets.

(A-2) Sustained Release Tablets

[1] A dispersant (e.g., hydrated silicon dioxide, light anhydrous silicic acid), a sustained-release base material (e.g., at least two components selected from hypromellose, a carboxyvinyl polymer, carboxymethylcellulose sodium salt, and the like) and other additives (e.g., microcrystalline cellulose) are blended into an unpulverized product of acetaminophen.

[2] The powder obtained in step [1] is deagglomerated and/or sized using a deagglomerating and/or sizing machine to disperse and make adhere the dispersant, the sustained-release base material and the other additives in and to the surfaces of acetaminophen particles uniformly.

[3] A lubricant (e.g., magnesium stearate) is blended into the powder obtained in step [2].

[4] The powder obtained in step [3] is deagglomerated and/or sized using a deagglomerating and/or sizing machine to disperse and make adhere all of the additives in and to the surfaces of acetaminophen particles uniformly, and the resultant product is compressed into tablets.

In the manufacturing method of the present invention, it is one of critical points that acetaminophen to be used is an unpulverized product. In drug substance manufacturers, acetaminophen is generally sold in the form of a product which is prepared by pulverizing large crystals generated during the production process or coarse particles generated as the result of secondary agglomeration using a pin mill, a hummer mill, or the like to adjust the particle diameters to a certain small value (where the product is also referred to as "a pulverized product of acetaminophen" or simply "a pulverized product" in the present invention). On the other hand, it is possible to get acetaminophen prepared by a process in which the above-mentioned pulverized step is eliminated (wherein the acetaminophen is also referred to as "unpulverized acetaminophen", "an unpulverized product of acetaminophen" or simply "an unpulverized product" in the present invention). In the present invention, a preparation is manufactured using the unpulverized product. The unpulverized product is manufactured by a process in which a pulverized step is eliminated, and therefore can be purchased at lower cost than pulverized products. Therefore, the cost for manufacture of the preparation can be reduced by manufacturing the preparation using the unpulverized product.

In addition, the unpulverized product of acetaminophen has larger particle diameters compared with the pulverized product of acetaminophen (the d50 value of the unpulverized product: about 120 to about 500 μm, the d50 value of the pulverized product: about 20 to 60 μm), and therefore does not undergo the generation of static electricity and has relatively good flowability and high handleability. Therefore, the unpulverized product has such an advantage that the manufacture of a preparation by a dry direct compression method can be achieved, which is often difficult to achieve using the pulverized product. However, when the particle diameter of a drug is large like the unpulverized product of acetaminophen, the total surface area of the drug is reduced and the elution rate may be deteriorated. In this case, the elution rate can be improved by adding a solubilizing agent as required.

The acetaminophen to be used in the manufacturing method of the present invention (also referred to as "the present acetaminophen") has a particle size distribution such that d10 is generally 5 to 300 μm, preferably 10 to 200 μm, more preferably 15 to 100 μm, and d90 is generally 200 to 900 μm, preferably 250 to 800 μm, more preferably 300 to 700 μm. Although there are some differences in the particle size distribution among lots, the unpulverized acetaminophen generally has the above-specified particle size distribution. In contrast, although there are some differences in the particle size distribution of a pulverized product of acetaminophen among the manufacturers of the drug substance and production lots, the particle size distribution of a pulverized product of acetaminophen is generally such that the d10 is 3 to 10 μm and d90 is 100 to 250 μm, and therefore the particle diameters of the pulverized product of acetaminophen are smaller compared with those of the present acetaminophen. In the present invention, the particle size distribution is determined by a volume distribution evaluation employing a laser-diffraction scattering method (Mastersizer 2000: Malvern), and the terms "d10", "d50", and "d90" refer to particle diameters at a volume cumulative 10% point, a volume cumulative 50% point, and a volume cumulative 90% point, respectively, as observed from the smaller diameter side in the particle size distribution.

In the present invention, the blending ratio of acetaminophen is not particularly limited, and is 90 to 99.9% by weight, preferably 95 to 99.7% by weight, more preferably 98 to 99.5% by weight, relative to 100% by weight of the premix drug substance of the present invention, and is 75 to 95% by weight, preferably 85 to 95% by weight, more preferably 87 to 93% by weight, relative to 100% by weight of a final preparation (e.g., tablets). For miniaturzing the tablets to improve the administerability of the tablets, it is preferred to increase the amount of a drug to be blended. However, it is important to avoid a case where the amount of the drug is too large and therefore the amounts of additives to be blended are limited to generate a disadvantage in the designing of the preparation. In the manufacturing method of the present invention, acetaminophen may be used singly, or acetaminophen may be combined with another pharmaceutically active ingredient appropriately depending on the types of diseases to be treated.

In the manufacturing method of the present invention, it is critical to use an unpulverized product of acetaminophen. It is more preferred to deagglomerate and/or size a powder prepared by mixing an unpulverized product of acetaminophen with additives using a deagglomerating and/or sizing machine to uniformly disperse and make adhere additives such as a dispersant and a solubilizing agent in and to the surfaces of acetaminophen particles. In the manufacturing method, the apparatus to be used for the deagglomeration and/or sizing is not particularly limited, and a deagglomerating and/or sizing machine which can make particles fine by the action to grind with a rod-shaped rotary body (number of rotations: about 800 rpm to 3000 rpm) is suitable. For example, a deagglomerating and/or sizing machine can be mentioned, which has such a function that an introduced raw material powder is deagglomerated by pressing the raw material powder against a tubular screen by the action of a centrifugal force generated by a rotating impeller (rotary vane), is spheronized on the impeller, and is then discharged through multiple openings provided in the screen. In the manufacturing method of the present invention, the screen diameter in the deagglomerating and/or sizing machine (i.e., the diameter of an opening in the screen) is preferably about 1 mm to 4 mm.

On the other hand, as a treatment for making particles fine like "deagglomeration", "pulverization" can be mentioned. A pulverizing machine is an apparatus in which a hammer or a pin rotates at a high rotation speed (number of rotation: about 5000 rpm to 15000 rpm) to make raw material powder particles fine by the action of compression, impact, friction, shear, and the like. Particularly, a pulverizing machine can treat particles regardless of the size of the particles. In general, in the case of acetaminophen, when acetaminophen is finely pulverized using a pulverizing machine such as pin mill, a hummer mill and a jet mill, small particles are pulverized excessively, and therefore the surface areas of the particles increase, and therefore the influence of electrostatic charging or an intermolecular force may increase. As a result, the flowability of the particles decreases to cause secondary agglomeration of the particles, and therefore the adhesion of the particles onto the inner wall surface of the apparatus or the like may occur, leading to the decrease in work efficiency.

For these reasons, in the manufacturing method of the present invention, it is critical to employ deagglomeration and/or sizing, rather than a commonly employed pulverization treatment, where the deagglomeration and/or sizing is such a treatment that coarse crystals and clusters of acetaminophen are selectively loosen finely and particles in a fine powder zone are not pulverized excessively and are dispersed uniformly to make a dispersion and the like adhere to the surfaces of the particles uniformly. In particularly, with respect to needle-like crystals having long and thin shapes among acetaminophen crystals, the crystals are deagglomerated and/or sized to adjust the particle diameters of the crystals so as to have a (major axis)/(minor axis) ratio of 3 or less. In this manner, the crystals can be dispersed more uniformly. As a result, the occurrence of electrostatic charging on acetaminophen or the generation of intermolecular forces in acetaminophen can be prevented and the flowability and agglomerating properties of the particles can be improved, resulting in further improvement in manufacturability. In particularly, the unpulverized product of acetaminophen used in the present invention contains large crystals that are generated in a crystallization step in the manufacturing process and clusters generated as the result of secondary agglomeration, and therefore has ununiform particle diameters compared with a pulverized product. Therefore, the deagglomerating and/or sizing treatment is preferred, because particle diameters can be adjusted by size-reducing acetaminophen particles having larger particle diameters selectively while preventing the excessive pulverization of acetaminophen particles having smaller particle diameters so as not to cause secondary agglomeration of the particles.

Examples of the dispersant to be used in the manufacturing method of the present invention include hydrated silicon dioxide, light anhydrous silicic acid, synthetic aluminum silicate, heavy anhydrous silicic acid, alumina magnesium hydroxide, magnesium aluminometasilicate, and dibasic calcium phosphate fine granulated, preferably hydrated silicon dioxide or light anhydrous silicic acid, more preferably hydrated silicon dioxide. These dispersants may be used singly, or any two or more of them may be used in combination.

The blending ratio of the dispersant in the present invention is not particularly limited, and is 0.1 to 3% by weight, preferably 0.3 to 1.5% by weight, relative to 100% by weight of the preparation.

In the case where a solubilizing agent is blended in the manufacturing method of the present invention, basically a powder solubilizing agent can be blended together with the dispersant. When it is intended to adjust the water content, it is possible to dissolve a solubilizing agent (e.g., Polysorbate 80 that has a liquid form) in water and add the resultant solution simultaneously with the adjustment of the water content. Examples of the solubilizing agent to be used in the manufacturing method of the present invention include: a powdery solubilizing agent, such as a macrogol powder, e.g., macrogol 4000, macrogol 6000, or macrogol 20000, and sodium lauryl sulfate, preferably macrogol 6000; and a liquid solubilizing agent, such as polysorbate 20, polysorbate 40, polysorbate 80, macrogol 200, and macrogol 400, preferably polysorbate 80. These solubilizing agents may be used singly, or any two or more of them may be used in combination.

The blending ratio of the solubilizing agent to be employed in the present invention is not particularly limited, and is 0 to 0.8% by weight, preferably 0 to 0.6% by weight, relative to 100% by weight of the preparation.

Examples of the excipient to be used in the manufacturing method of the present invention include a sugar (e.g., lactose, glucose, fructose, sucrose), a sugar alcohol (D-mannitol), microcrystalline cellulose, powdered cellulose, corn starch, potato starch, partly pregelatinized starch, sodium carboxymethyl starch, dextrin, ß-cyclodextrin, carmellose sodium, light anhydrous silicic acid, hydrated silicon dioxide, silicon dioxide, precipitated calcium carbonate, anhydrous dibasic calcium phosphate, magnesium oxide, titanium oxide, calcium lactate, magnesium aluminate metasilicate, synthetic hydrotalcite, talc, and kaolin, preferably microcrystalline cellulose. These excipients may be used singly, or any two or more of them may be used in combination.

The blending ratio of the excipient, particularly microcrystalline cellulose, in the present invention is not particularly limited, and is 1 to 10% by weight, preferably 2 to 8% by weight, more preferably 2.5 to 6% by weight, relative to 100% by weight of the preparation excluding the premix drug substance.

Examples of the disintegrating agent to be used in the manufacturing method of the present invention include carboxymethylcellulose (e.g., carmellose, carmellose sodium, carmellose calcium, croscarmellose sodium, microcrystalline cellulose-carmellose sodium), carboxymethyl starch (e.g., carboxymethyl starch, sodium carboxymethyl starch (e.g., sodium starch glycolate)), crospovidone, low substituted hydroxypropylcellulose, low substituted sodium hydroxymethyl starch, starch (e.g., partly pregelatinized starch, corn starch, potato starch), alginic acid, and bentonite. The disintegrating agent is preferably crospovidone, low substituted hydroxypropylcellulose, sodium carboxymethyl starch, or partly pregelatinized starch, more preferably crospovidone or low substituted hydroxypropylcellulose, particularly preferably low substituted hydroxypropylcellulose. These disintegrating agents may be used singly, or any two or more of them may be used in combination.

The blending ratio of the disintegrating agent in the present invention is not particularly limited, and is 0 to 10% by weight, preferably 1 to 10% by weight, more preferably 2 to 8% by weight, still more preferably 3 to 6% by weight, relative to 100% by weight of the preparation excluding the premix drug substance.

The sustained-release base material to be used in the manufacturing method of the present invention is preferably one which, when contacting with water, can form a hydrogel to control the release of a drug therefrom. Examples of the sustained-release base material include: a cellulose derivative such as hydroxypropylcellulose (a high-viscosity grade), methylcellulose, hypromellose (hydroxypropylmethylcellulose), carboxymethylcellulose, carboxymethylcellulose sodium, and carboxymethylethylcellulose; a carboxyvinyl polymer; and sodium alginate. The sustained-release base material is preferably hypromellose, carboxymethylcellulose sodium, or a carboxyvinyl polymer, more preferably hypromellose or a carboxyvinyl polymer. These sustained-release base materials may be used singly. Preferably a combination of at least two of these sustained-release base materials is used to adjust the preparation so as to exert desired sustained release properties.

The amount of the sustained-release base material to be blended is not particularly limited, and is 0 to 15% by weight, preferably 1 to 15% by weight, more preferably 2 to 10% by weight, still more preferably 3 to 8% by weight, especially more preferably 4 to 6% by weight, relative to 100% by weight of the preparation excluding the premix drug substance.

Examples of the lubricant to be used in the manufacturing method of the present invention include stearic acid, magnesium stearate, calcium stearate, talc, sucrose esters of fatty acids, glycerol esters of fatty acids, a hydrogenated oil, polyethylene glycol, dimethyl polysiloxane, carnauba wax, sodium lauryl sulfate, yellow beeswax, and white beeswax, preferably magnesium stearate. These lubricants may be used singly, or any two or more of them may be used in combination.

The blending ratio of the lubricant in the present invention is not particularly limited, and is 0.05 to 1% by weight, preferably 0.1 to 0.5% by weight, relative to 100% by weight of the preparation.

In the manufacturing method of the present invention, various additives other than the above-mentioned additives, which can be commonly used in the manufacture of preparations, can also be blended appropriately depending on the intended use, as long as the advantages of the present invention cannot be deteriorated. Examples of the additive other than the above-mentioned additives include a binder, an antioxidant, a preservative, a surfactant, a plasticizer, a pH modifier (e.g., sodium hydrogen carbonate), a coloring agent, a flavoring agent, a sweetening agent, a foaming agent, and a fragrance.

Specific examples of the binder include a polyvinyl alcohol-acrylic acid-methyl methacrylate copolymer (e.g., POVACOAT [registered tradename: the same applies hereafter]), hydroxypropylcellulose (a low-viscosity grade), gelatin, hydroxypropylmethylcellulose, polyvinylpyrrolidone, a polyvinyl alcohol-polyethylene glycol-graft copolymer, an ethyl acrylate-methyl methacrylate copolymer, and corn starch. Among these binders, those which have high molecular weights can also be used as solubilizing agents.

EXAMPLES

The present invention will be described specifically with reference to examples. However, the present invention is not intended to be limited by these examples. Comil QC-197S (manufactured by Powrex Corporation) was used as a deagglomerating and/or sizing machine, and a rotary tablet pressing machine model-VEL5 (manufactured by KIKUSUI SEISAKUSHO LTD.) was used as a tablet pressing machine.

(A) Tablet Manufacture Example
[A-1: Conventional Tablets]

Example 1

An unpulverized product of acetaminophen (455.0 g) was mixed with hydrated silicon dioxide (Carplex [registered tradename: the same applies hereafter]) (2.5 g), the resultant mixture was deagglomerated and/or sized and uniformly dispersed using a deagglomerating and/or sizing machine (screen diameter: 1 mm) to produce a powder, and then microcrystalline cellulose (CEOLUS [registered tradename: the same applies hereafter] KG-1000) (16.0 g) and low substituted hydroxypropylcellulose (L-HPC NBD-021) (25.0 g) were added to and mixed with the powder. Water in an amount of about 1% by weight relative to the whole amount of the powder (i.e., about 5 g) was added to and mixed with the resultant mixture using an atomizer. Magnesium stearate (1.5 g) was added to the mixture, and the resultant mixture was compressed into tablets using a tablet pressing machine (compression pressure: 10 kN) to produce tablets each having hardness of 60 N.

| [Components in tablets (blended amounts)] | [Content (% by weight)] |
|---|---|
| Acetaminophen (455.0 g) | 91.0% |
| Hydrated silicon dioxide (2.5 g) | 0.5% |
| Microcrystalline cellulose (16.0 g) | 3.2% |
| L-HPC (25.0 g) | 5.0% |
| Water content adjustment | |
| Magnesium stearate (1.5 g) | 0.3% |

Total: 500.0 g, water content: 1.0%

Example 2

An unpulverized product of acetaminophen (455.0 g) was mixed with hydrated silicon dioxide (Carplex [registered tradename: the same applies hereafter]) (2.5 g), the resultant mixture was deagglomerated and/or sized and uniformly dispersed using a deagglomerating and/or sizing machine (screen diameter: 1 mm) to produce a powder, and then microcrystalline cellulose (CEOLUS [registered tradename: the same applies hereafter] KG-1000) (16.0 g) and crospovidone (Ultra-10) (25.0 g) were added to and mixed with the powder. Water in an amount of about 1% by weight relative to the whole amount of the powder (i.e., about 5 g) was added to and mixed with the resultant mixture using an atomizer. Magnesium stearate (1.5 g) was added to the mixture, and the resultant mixture was compressed into tablets using a tablet pressing machine (compression pressure: 10 kN) to produce tablets each having hardness of 50 N.

| [Components in tablets (blended amounts)] | [Content (% by weight)] |
|---|---|
| Acetaminophen (455.0 g) | 91.0% |
| Hydrated silicon dioxide (2.5 g) | 0.5% |
| Microcrystalline cellulose (16.0 g) | 3.2% |
| Crospovidone (25.0 g) | 5.0% |
| Water content adjustment | |
| Magnesium stearate (1.5 g) | 0.3% |

Total: 500.0 g, water content: 1.0%

Example 3

An unpulverized product of acetaminophen (300.0 g), hydrated silicon dioxide (Carplex) (1.5 g) and macrogol 6000 powder (1.5 g) were deagglomerated and/or sized together and uniformly dispersed using a deagglomerating and/or sizing machine to produce a powder, and then microcrystalline cellulose (CEOLUS KG-1000) (25.0 g) and low substituted hydroxypropylcellulose (15.0 g) were added to and mixed with the powder. Water in an amount of about 1.5% by weight relative to the whole amount of the powder was added to and mixed with the resultant mixture using an atomizer to adjust the water content, and then a polyvinyl alcohol-acrylic acid-methyl methacrylate copolymer (POVACOAT) (6.5 g) and D-mannitol (Parteck [registered tradename: the same applies hereafter] M) (15.0 g) were added to the mixture, and the resultant mixture was deagglomerated and/or sized and uniformly dispersed. Magnesium stearate (2.0 g) was added to the mixture, and the resultant mixture was compressed into tablets using a tablet pressing machine (compression pressure: 14 kN) to produce tablets each having hardness of 65 N.

| [Components in tablets (blended amounts)] | [Content (% by weight)] |
|---|---|
| Acetaminophen (300.0 g) | 82.2% |
| Hydrated silicon dioxide (1.5 g) | 0.4% |
| Macrogol 6000 powder (1.5 g) | 0.4% |
| Microcrystalline cellulose (23.5 g) | 6.4% |
| L-HPC (15.0 g) | 4.1% |
| Water content adjustment | |
| POVACOAT (6.5 g) | 1.8% |
| D-mannitol (15.0 g) | 4.1% |
| Magnesium stearate (2.0 g) | 0.5% |

Total: 365.0 g, water content: 1.5%

Example 4

An unpulverized product of acetaminophen (300.0 g) and light anhydrous silicic acid (AEROSIL [registered tradename: the same applies hereafter]) (1.5 g) were deagglomerated and/or sized together and uniformly dispersed using a deagglomerating and/or sizing machine to produce a powder, and then microcrystalline cellulose (CEOLUS KG-1000) (25.0 g) was added to and mixed with the powder. Water in an amount of about 1.5% by weight relative to the whole amount of the powder was added to and mixed with the resultant mixture using an atomizer to adjust the water content, and then D-mannitol (Parteck M) (15.0 g) was added to the mixture, and the resultant mixture was deagglomerated and/or sized and uniformly dispersed. Magnesium stearate (2.0 g) was added to the mixture, and the resultant mixture was compressed into tablets using a tablet pressing machine (compression pressure: 14 kN) to produce tablets each having hardness of 62 N.

| [Components in tablets (blended amounts)] | [Content (% by weight)] |
| --- | --- |
| Acetaminophen (300.0 g) | 87.3% |
| Light anhydrous silicic acid (1.5 g) | 0.4% |
| Microcrystalline cellulose (25.0 g) | 7.3% |
| Water content adjustment | |
| D-mannitol (15.0 g) | 4.4% |
| Magnesium stearate (2.0 g) | 0.6% |

Total: 343.5g, water content: 1.5%

Example 5

An unpulverized product of acetaminophen (300.0 g) and hydrated silicon dioxide (Carplex) (1.5 g) were deagglomerated and/or sized together and uniformly dispersed using a deagglomerating and/or sizing machine to produce a powder, and then microcrystalline cellulose (CEOLUS KG-1000) (25.0 g) was added to and mixed with the powder. Water in an amount of about 1.5% by weight relative to the whole amount of the powder was added to and mixed with the resultant mixture using an atomizer to adjust the water content, and then D-mannitol (Parteck M) (13.0 g) was added to the mixture, and the resultant mixture was deagglomerated and/or sized and uniformly dispersed. Magnesium stearate (2.0 g) was added to the mixture, and the resultant mixture was compressed into tablets using a tablet pressing machine (compression pressure: 14 kN) to produce tablets each having hardness of 69 N.

| [Components in tablets (blended amounts)] | [Content (% by weight)] |
| --- | --- |
| Acetaminophen (300.0 g) | 87.8% |
| Hydrated silicon dioxide (1.5 g) | 0.4% |
| Microcrystalline cellulose (25.0 g) | 7.3% |
| Water content adjustment | |
| D-mannitol (13.0 g) | 3.8% |
| Magnesium stearate (2.0 g) | 0.6% |

Total: 341.5 g, water content: 1.5%

Example 6

An unpulverized product of acetaminophen (300.0 g), hydrated silicon dioxide (Carplex) (1.5 g), and macrogol 6000 powder (1.5 g) were deagglomerated and/or sized together and uniformly dispersed using a deagglomerating and/or sizing machine to produce a powder, and then microcrystalline cellulose (CEOLUS KG-1000) (35.0 g) was added to and mixed with the powder. Water in an amount of about 1.5% by weight relative to the whole amount of the powder was added to and mixed with the resultant mixture using an atomizer to adjust the water content, and then trehalose (30.0 g) was added to the mixture, and the resultant mixture was deagglomerated and/or sized and uniformly dispersed. Magnesium stearate (2.0 g) was added to the mixture, and the resultant mixture was compressed into tablets using a tablet pressing machine (compression pressure: 14 kN) to produce tablets each having hardness of 75 N.

| [Components in tablets (blended amounts)] | [Content (% by weight)] |
| --- | --- |
| Acetaminophen (300.0 g) | 81.4% |
| Hydrated silicon dioxide (1.5 g) | 0.4% |
| Macrogol 6000 powder (1.5 g) | 0.4% |
| Microcrystalline cellulose (35.0 g) | 9.5% |
| Water content adjustment | |
| Trehalose (28.5 g) | 7.9% |
| Magnesium stearate (2.0 g) | 0.5% |

Total: 368.5 g, water content: 1.5%

Example 7

An unpulverized product of acetaminophen (300.0 g) and hydrated silicon dioxide (Carplex) (1.5 g) were deagglomerated and/or sized together and uniformly dispersed using a deagglomerating and/or sizing machine to produce a powder, and then microcrystalline cellulose (CEOLUS KG-1000) (35.0 g) was added to and mixed with the powder. Water in an amount of about 2.0% by weight relative to the whole amount of the powder was added to and mixed with the resultant mixture using an atomizer to adjust the water content, and then D-mannitol (Mannit P) (25.0 g) was added to the mixture, and the resultant mixture was deagglomerated and/or sized and uniformly dispersed. Magnesium stearate (2.0 g) was added to the mixture, and the resultant mixture was compressed into tablets using a tablet pressing machine (compression pressure: 14 kN) to produce tablets each having hardness of 87 N.

| [Components in tablets (blended amounts)] | [Content (% by weight)] |
| --- | --- |
| Acetaminophen (300.0 g) | 82.5% |
| Hydrated silicon dioxide (1.5 g) | 0.4% |
| Microcrystalline cellulose (35.0 g) | 9.6% |
| Water content adjustment | |
| D-mannitol (25.0 g) | 6.9% |
| Magnesium stearate (2.0 g) | 0.6% |

Total: 363.5 g, water content = 2.0%

Example 8

An unpulverized product of acetaminophen (300.0 g) and hydrated silicon dioxide (Carplex) (1.6 g) were deagglomerated and/or sized and uniformly dispersed using a deagglomerating and/or sizing machine to produce a powder, and then microcrystalline cellulose (CEOLUS KG-1000) (22.0 g) and low substituted hydroxypropylcellulose (5.0 g) were added to and mixed with the powder. Water in an amount of about 1.5% by weight relative to the whole amount of the powder was added to and mixed with the resultant mixture using an atomizer. Magnesium stearate (2.0 g) was added to the mixture, and the resultant mixture was compressed into tablets using a tablet pressing machine (compression pressure: 14 kN) to produce tablets each having hardness of 55 N.

| [Components in tablets (blended amounts)] | [Content (% by weight)] |
|---|---|
| Acetaminophen (300.0 g) | 90.7% |
| Hydrated silicon dioxide (1.6 g) | 0.5% |
| Microcrystalline cellulose (22.0 g) | 6.7% |
| L-HPC (5.0 g) | 1.5% |
| Water content adjustment | |
| Magnesium stearate (2.0 g) | 0.6% |

Total: 330.6 g, water content = 1.5%

Example 9

An unpulverized product of acetaminophen (300.0 g) and hydrated silicon dioxide (Carplex) (1.6 g) were deagglomerated and/or sized together and uniformly dispersed using a deagglomerating and/or sizing machine to produce a powder, and then microcrystalline cellulose (CEOLUS KG-1000) (22.0 g) and low substituted hydroxypropylcellulose (6.0 g) were added to and mixed with the powder. Water in an amount of about 2.0% by weight relative to the whole amount of the powder was added to the resultant mixture using an atomizer to adjust the water content, and then D-mannitol (Mannit P) (25.0 g) was added to the mixture, and the resultant mixture was deagglomerated and/or sized and uniformly dispersed. Magnesium stearate (2.0 g) was added to the mixture, and the resultant mixture was compressed into tablets using a tablet pressing machine (compression pressure: 14 kN) to produce tablets each having hardness of 50 N.

| [Components in tablets (blended amounts)] | [Content (% by weight)] |
|---|---|
| Acetaminophen (300.0 g) | 84.1% |
| Carplex (1.6 g) | 0.4% |
| Microcrystalline cellulose (22.0 g) | 6.2% |
| L-HPC (6.0 g) | 1.7% |
| Water content adjustment | |
| Mannit P (25.0 g) | 7.0% |
| Magnesium stearate (2.0 g) | 0.6% |

Total: 356.6 g, water content = 2.0%

[A-2: Sustained Release Tablets]

Example 10

Hydrated silicon dioxide (Carplex) (5.0 g), hypromellose (METOLOSE 90SH1000000 SR) (15.0 g), a carboxyvinyl polymer (Carbopol 971 PNF) (10.0 g), and microcrystalline cellulose (CEOLUS KG-1000) (25.0 g) were added to and mixed with an unpulverized product of acetaminophen (450.0 g), and the resultant mixture was deagglomerated and/or sized and uniformly dispersed using a deagglomerating and/or sizing machine (screen diameter: 2 mm). Magnesium stearate (2.5 g) was added to the resultant product, and the resultant mixture was deagglomerated and/or sized and uniformly dispersed and was then compressed into tablets using a tablet pressing machine (compression pressure: 10 kN) to produce tablets each having hardness of 45N.

| [Components in tablets (blended amounts)] | [Content (% by weight)] |
|---|---|
| Acetaminophen (450.0 g) | 88.7% |
| Hydrated silicon dioxide (5.0 g) | 1.0% |
| Hypromellose (15.0 g) | 3.0% |
| Carboxyvinyl polymer (10.0 g) | 2.0% |
| Microcrystalline cellulose (25.0 g) | 4.9% |
| Magnesium stearate (2.5 g) | 0.5% |

Total: 507.5 g

Example 11

An unpulverized product of acetaminophen (398.0 g) and light anhydrous silicic acid (AEROSIL) (2.0 g) were deagglomerated and/or sized together and uniformly dispersed using a deagglomerating and/or sizing machine to produce a powder, and then microcrystalline cellulose (CEOLUS KG-1000) (50.0 g) was added to and mixed with the powder. Water in an amount of about 1.8% by weight relative to the whole amount of the powder was added to and mixed with the resultant mixture using an atomizer to adjust the water content, and then a carboxyvinyl polymer (80.0 g) was added to the mixture, and the resultant mixture was deagglomerated and/or sized and uniformly dispersed. Magnesium stearate (2.5 g) was added to the mixture, and the resultant mixture was compressed into tablets using a tablet pressing machine (compression pressure: 14 kN) to produce tablets each having hardness of 71 N.

| [Components in tablets (blended amounts)] | [Content (% by weight)] |
|---|---|
| Acetaminophen (398.0 g) | 74.7% |
| AEROSIL (2.0 g) | 0.4% |
| Microcrystalline cellulose (50.0 g) | 9.4% |
| Water content adjustment | |
| Carboxyvinyl polymer (80.0 g) | 15.0% |
| Magnesium stearate (2.5 g) | 0.5% |

Total: 532.5 g, water content = 1.8%

Example 12

An unpulverized product of acetaminophen (300.0 g) and hydrated silicon dioxide (Carplex) (1.5 g) were deagglomerated and/or sized together and uniformly dispersed using a deagglomerating and/or sizing machine to produce a powder, and then microcrystalline cellulose (CEOLUS KG-1000) (32.0 g) was added to and mixed with the powder. Water in an amount of about 1.8% by weight relative to the whole amount of the powder was added to and mixed with the resultant mixture using an atomizer to adjust the water content, and then a carboxyvinyl polymer (25.0 g), hydroxypropylcellulose (SSL) (7.0 g), and trehalose (15.0 g) were added to the mixture, and the resultant mixture was deagglomerated and/or sized and uniformly dispersed. Magnesium stearate (2.0 g) was added to the mixture, and the resultant mixture was compressed into tablets using a tablet pressing machine (compression pressure: 14 kN) to produce tablets each having hardness of 89 N.

| [Components in tablets (blended amounts)] | [Content (% by weight)] |
|---|---|
| Acetaminophen (300.0 g) | 78.4% |
| Hydrated silicon dioxide (1.5 g) | 0.4% |

-continued

| [Components in tablets (blended amounts)] | [Content (% by weight)] |
|---|---|
| Microcrystalline cellulose (32.0 g) | 8.4% |
| Water content adjustment | |
| Carboxyvinyl polymer (25.0 g) | 6.5% |
| HPC (7.0 g) | 1.8% |
| Trehalose (15.0 g) | 3.9% |
| Magnesium stearate (2.0 g) | 0.5% |

Total: 382.5 g, water content = 1.8%

Example 13

An unpulverized product of acetaminophen (300.0 g) and light anhydrous silicic acid (AEROSIL) (1.5 g) were deagglomerated and/or sized together and uniformly dispersed using a deagglomerating and/or sizing machine to produce a powder, and then a carboxyvinyl polymer (55.0 g), microcrystalline cellulose (CEOLUS KG-1000) (5.0 g), and trehalose (5.0 g) were added to the mixture, and the resultant mixture was deagglomerated and/or sized and uniformly dispersed. Magnesium stearate (8.5 g) was added to the mixture, and the resultant mixture was compressed into tablets using a tablet pressing machine (compression pressure: 10 kN) to produce tablets each having hardness of 43 N.

| [Components in tablets (blended amounts)] | [Contents (% by weight)] |
|---|---|
| Acetaminophen (300.0 g) | 80.0% |
| Light anhydrous silicic acid (1.5 g) | 0.4% |
| Carboxyvinyl polymer (55.0 g) | 14.7% |
| Microcrystalline cellulose (5.0 g) | 1.3% |
| Trehalose (5.0 g) | 1.3% |
| Magnesium stearate (8.5 g) | 2.3% |

Total: 375.0 g

Example 14

An unpulverized product of acetaminophen (300.0 g) and light anhydrous silicic acid (AEROSIL) (1.5 g) were deagglomerated and/or sized together and uniformly dispersed using a deagglomerating and/or sizing machine to produce a powder, then a carboxyvinyl polymer (50.0 g) was added to the powder, the resultant mixture was deagglomerated and/or sized and uniformly dispersed, and then microcrystalline cellulose (CEOLUS KG-1000) (7.0 g) and trehalose (8.0 g) were added to the mixture, and the resultant mixture was uniformly dispersed. Magnesium stearate (8.5 g) was added to the mixture, and the resultant mixture was compressed into tablets using a tablet pressing machine (compression pressure: 10 kN) to produce tablets each having hardness of 46 N.

| [Components in tablets (blended amounts)] | [Contents (% by weight)] |
|---|---|
| Acetaminophen (300.0 g) | 80.0% |
| Light anhydrous silicic acid (1.5 g) | 0.4% |
| Carboxyvinyl polymer (50.0 g) | 13.3% |
| Microcrystalline cellulose (7.0 g) | 1.9% |
| Trehalose (8.0 g) | 2.1% |
| Magnesium stearate (8.5 g) | 2.3% |

Total: 375.0 g

Example 15

An unpulverized product of acetaminophen (300.0 g) and hydrated silicon dioxide (Carplex) (1.5 g) were deagglomerated and/or sized together and uniformly dispersed using a deagglomerating and/or sizing machine to produce a powder, then a carboxyvinyl polymer (45.0 g) was added to the powder, the resultant mixture was deagglomerated and/or sized and uniformly dispersed, and then microcrystalline cellulose (CEOLUS KG-1000) (17.0 g) was added to the mixture, and the resultant mixture was uniformly dispersed. Magnesium stearate (8.5 g) was added to the mixture, and the resultant mixture was compressed into tablets using a tablet pressing machine (compression pressure: 10 kN) to produce tablets each having hardness of 47 N.

| [Components in tablets (blended amounts)] | [Contents (% by weight)] |
|---|---|
| Acetaminophen (300.0 g) | 80.6% |
| Hydrated silicon dioxide (1.5 g) | 0.4% |
| Carboxyvinyl polymer (45.0 g) | 12.1% |
| Microcrystalline cellulose (17.0 g) | 4.6% |
| Magnesium stearate (8.5 g) | 2.3% |

Total: 372.0 g

Example 16

An unpulverized product of acetaminophen (300.0 g) and hydrated silicon dioxide (Carplex) (1.5 g) were deagglomerated and/or sized together and uniformly dispersed using a deagglomerating and/or sizing machine to produce a powder, then a carboxyvinyl polymer (40.0 g) was added to the powder, the resultant mixture was deagglomerated and/or sized and uniformly dispersed, and then hydroxypropylcellulose (SSL) (15.0 g) and trehalose (10.0 g) were further added to the mixture, and the resultant mixture was uniformly dispersed. Magnesium stearate (8.5 g) was added to the mixture, and the resultant mixture was compressed into tablets using a tablet pressing machine (compression pressure: 10 kN) to produce tablets each having hardness of 49 N.

| [Components in tablets (blended amounts)] | [Contents (% by weight)] |
|---|---|
| Acetaminophen (300.0 g) | 80.0% |
| Hydrated silicon dioxide (1.5 g) | 0.4% |
| Carboxyvinyl polymer (40.0 g) | 10.7% |
| HPC (SSL) (15.0 g) | 4.0% |
| Trehalose (10.0 g) | 2.7% |
| Magnesium stearate (8.5 g) | 2.3% |

Total: 375.0 g

Example 17

An unpulverized product of acetaminophen (300.0 g) and hydrated silicon dioxide (Carplex) (1.5 g) were deagglomerated and/or sized together and uniformly dispersed using a deagglomerating and/or sizing machine to produce a powder, then a carboxyvinyl polymer (35.0 g) was added to the powder, the resultant mixture was deagglomerated and/or sized and uniformly dispersed, and then microcrystalline cellulose (CEOLUS KG-1000) (15.0 g) and D-mannitol (15.0 g) were further added to the mixture, and the resultant mixture was uniformly dispersed. Magnesium stearate (8.5 g) was added to the mixture, and the resultant mixture was compressed into tablets using a tablet pressing machine (compression pressure: 10 kN) to produce tablets each having hardness of 46 N.

| [Components in tablets (blended amounts)] | [Contents (% by weight)] |
|---|---|
| Acetaminophen (300.0 g) | 80.0% |
| Hydrated silicon dioxide (1.5 g) | 0.4% |
| Carboxyvinyl polymer (35.0 g) | 9.3% |
| Microcrystalline cellulose (15.0 g) | 4.0% |
| D-mannitol (15.0 g) | 4.0% |
| Magnesium stearate (8.5 g) | 2.3% |

Total: 375.0 g (B) Production Example of Premix Drug Substance

Example 18

An unpulverized product of acetaminophen (398.0 g) was added to light anhydrous silicic acid (AEROSIL) (2.0 g), and the mixture was deagglomerated and/or sized together and uniformly dispersed using a deagglomerating and/or sizing machine (screen diameter: 3.9 mm) to produce a powder, which was used as a premix drug substance. As an evaluation index for the flowability of a powder, the premix drug substance thus manufactured was dropped from a funnel or the like and an angle between a slope and a horizontal plane of an accumulated circular cone of the premix drug substance was measured as an angle of repose. As a result, the angle of repose of the premix drug substance was 38 degrees. The angle of repose became smaller with the increase in flowability and became larger with the decrease in flowability. The adhesion of the powder onto the inner surface of the apparatus was also reduced greatly, and the collection rate was 97%.

| [Components in premix drug substance (blended amounts)] | [Contents (% by weight)] |
|---|---|
| Acetaminophen (398.0 g) | 99.5% |
| Light anhydrous silicic acid (2.0 g) | 0.5% |

Example 19

An unpulverized product of acetaminophen (398.0 g) was added to hydrated silicon dioxide (Carplex) (2.0 g) and macrogol 6000 powder (2.0 g), and the mixture was deagglomerated and/or sized together and uniformly dispersed using a deagglomerating and/or sizing machine (screen diameter: 1.99 mm) to produce a powder, which was used as a premix drug substance. The angle of repose of the premix drug substance was measured in the same manner as in Example 18. As a result, the angle of repose was 36 degrees. The adhesion of the powder onto the inner surface of the apparatus was also reduced greatly, and the collection rate was 98%.

| [Components in premix drug substance (blended amounts)] | [Contents (% by weight)] |
|---|---|
| Acetaminophen (398.0 g) | 99.0% |
| Hydrated silicon dioxide (2.0 g) | 0.5% |
| Macrogol 6000 powder (2.0 g) | 0.5% |

COMPARATIVE EXAMPLES

Comparative Example 1

It was tried to introduce only an acetaminophen pulverized product (300.0 g) into a Ro-tap-type particle size distribution measurement machine and to perform the measurement. However, the screen was clogged immediately due to the electrostatic charging caused by vibration and it was impossible to perform the measurement.

Comparative Example 2

Microcrystalline cellulose (CEOLUS KG-1000) (15.0 g) was added to an acetaminophen pulverized product (300.0 g), and the resultant mixture was dispersed uniformly using a rotary drum-type mixer to produce a mixed powder. The angle of repose of the premix drug substance thus manufactured was measured in the same manner as in Example 18. As a result, the angle of repose was 45 degrees. The amount of the powder adhering to the inner surface of the apparatus was large, a large amount of fine powder particles spread during the operation of recovering the adhering powder, the collection rate was 95%, and each recovery operation was difficult.

| [Components in mixed powder (blended amounts)] | [Contents (% by weight)] |
|---|---|
| Acetaminophen pulverized product (300.0 g) | 95.2% |
| Microcrystalline cellulose (15.0 g) | 4.8% |

Comparative Example 3

Microcrystalline cellulose (UF702: Asahi Kasei Chemicals Corporation) (65.0 g) and magnesium stearate (8.5 g) were added to a powder in which a pulverized product of acetaminophen (300.0 g) and light anhydrous silicic acid (AEROSIL) (1.5 g) were dispersed uniformly, and the resultant mixture was compressed into tablets using a tablet pressing machine (compression pressures: 10 kN and 12 kN). However, the hardness of the tablets was low (12 N) and capping occurred. Therefore, it was difficult to perform the evaluation and the packaging of the tablets was also impossible.

| [Components in tablets (blended amounts)] | [Contents (% by weight)] |
|---|---|
| Acetaminophen (300.0 g) | 80.0% |
| Light anhydrous silicic acid (1.5 g) | 0.4% |
| Microcrystalline cellulose (65.0 g) | 17.3% |
| Magnesium stearate (8.5 g) | 2.3% |

Total: 375.0 g

TEST EXAMPLE 1: MEASUREMENT OF PARTICLE SIZE DISTRIBUTION OF ACETAMINOPHEN

Each of unpulverized products of acetaminophen (lots A to D) and a pulverized product of acetaminophen (lot P) was subjected to a particle size distribution measurement using a particle measurement method (a dry mode measurement) by a laser-diffraction method. As a machine, a dry automated dispersion unit microtray (Mastersizer 2000, Malvern) was used, the dispersion compression air pressure was 2 Bar, and the analysis of particle size distribution was performed by a volume conversion method. One example of the results is shown in Table 1. The results of lots E, F, Q, and R are data which were obtained by another company using a different measurement apparatus under different measurement conditions from those employed in the test of the present invention. As shown in the results of Table 1, difference may sometimes occur depending on the measurement conditions and measurement apparatuses used in the measurement of particle size distribution.

TABLE 1

| Acetaminophen Drug Substance | | D10 (μm) | D90 (μm) |
|---|---|---|---|
| Unpulverized Product | Lot A | 20 | 320 |
| | Lot B | 30 | 551 |
| | Lot C | 26 | 419 |
| | Lot D | 20 | 464 |
| | Lot E | 93 | 559 |
| | Lot F | 220 | 663 |
| Pulverized Product | Lot P | 3.7 | 166 |
| | Lot Q | 5.8 | 104 |
| | Lot R | 9.7 | 192 |

TEST EXAMPLE 2: ELUTION TEST

The acetaminophen tablets (acetaminophen content: 300 mg/tablet) manufactured in Example 1 were subjected to an elution test by a method in accordance with the second method (paddle method) in Japanese Pharmacopoeia (abbreviated as "JP", hereinafter) general test method/elution test method. As a test solution, water mentioned in the JP general test method/disintegration test method was used.

One test tablet was put into a test solution (900 mL) that was kept at a liquid temperature of 37±0.5° C., and the elution test started at 50 rpm/min. Subsequently, an eluate (10 mL) was collected at fixed time intervals and was then filtered through a membrane filter having a pore size of 0.45 μm to produce a sample solution. A portion (10 μL) of the sample solution was subjected to the measurement of the elution amount of acetaminophen by high performance liquid chromatography (HPLC). The HPLC was performed under the following conditions: a photodiode array detector (measurement wavelength: 287 nm), column [ODS (length: about 15 cm× inner diameter: about 4.6 mm)], column temperature [about 35° C.], mobile phase [pH 6.8 phosphate buffer/acetonitrile (7:3)] and flow rate [1.0 mL/min]. One example of the results of the elution test until 30 minutes after the elution is shown in FIG. 1.

As shown in the graph in FIG. 1, the preparation manufactured by the manufacturing method of the present invention exerted excellent elution behavior, and showed an elution rate of 87.6%, which meets the official elution test standard described in Japanese Pharmaceutical Codex, part 3, i.e., an elution rate of 80% or more within 15 minutes.

INDUSTRIAL APPLICABILITY

According to the manufacturing method of the present invention, it becomes possible to improve the flowability of acetaminophen and minimize the amount of an additive to be added for the preparation. As a result, a preparation having improved QOL and compliance, such as acetaminophen tablets that are miniaturized and have improved administerability and acetaminophen sustained-release tablets of which the number of doses per day is reduced compared with the conventional preparations, can be manufactured by a dry direct compression method that is the simplest method. Therefore, the time of manufacturing is shortened to improve the manufacturing efficiency, and the cost for manufacturing is also reduced. Therefore, the manufacturing method is very useful and is suitable for practical use.

The invention claimed is:

1. A method for manufacturing a premix drug substance, wherein the method includes the steps of blending a dispersant in an amount of 0.1 to 3% relative to 100% by weight of the premix drug substance and optionally a solubilizing agent in an amount of 0 to 0.8% by weight relative to 100% by weight of the premix drug substance into unpulverized acetaminophen having a particle size distribution that d10 is 5 to 300 μm, d50 is about 120 to about 500 μm, and d90 is 200 to 900 μm in an amount of 90 to 99.9% by weight relative to 100% by weight of the premix drug substance; and then carrying out deagglomeration and/or sizing to disperse and make adhere the dispersant, or the dispersant and the solubilizing agent in and onto the surfaces of the acetaminophen particles uniformly to make powder and wherein the process prevents deterioration of agglomeration and poor flowability, wherein the dispersant is at least one of hydrated silicon dioxide or light anhydrous silicic acid.

2. The manufacturing method according to claim 1, wherein the acetaminophen has the particle size distribution that d10 is 10 to 200 μm and d90 is 250 to 800 μm.

3. The manufacturing method according to claim 1, wherein the dispersant is hydrated silicon dioxide.

4. The manufacturing method according to claim 1, wherein the solubilizing agent is macrogol or sodium lauryl sulfate.

* * * * *